(12) United States Patent
Sun et al.

(10) Patent No.: US 12,033,762 B2
(45) Date of Patent: Jul. 9, 2024

(54) METHOD OF NON-INTERACTIVE ZERO-KNOWLEDGE CROWD VERIFIABLE DIGITAL CONTACT TRACING

(71) Applicants: Sheng Sun, Ottawa (CA); Wen Tong, Ottawa (CA)

(72) Inventors: Sheng Sun, Ottawa (CA); Wen Tong, Ottawa (CA)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 251 days.

(21) Appl. No.: 17/732,071

(22) Filed: Apr. 28, 2022

(65) Prior Publication Data

US 2023/0352189 A1 Nov. 2, 2023

(51) Int. Cl.
*G16H 50/80* (2018.01)
*H04L 9/00* (2022.01)
*H04L 9/32* (2006.01)

(52) U.S. Cl.
CPC .......... *G16H 50/80* (2018.01); *H04L 9/3218* (2013.01); *H04L 9/50* (2022.05)

(58) Field of Classification Search
CPC .......... G16H 50/80; H04L 9/50; H04L 9/3218
See application file for complete search history.

(56) References Cited

U.S. PATENT DOCUMENTS

| 10,887,104 B1* | 1/2021 | Jayachandran | ....... H04L 9/3239 |
| 2021/0337355 A1* | 10/2021 | Sobol | ..................... H04W 4/023 |
| 2021/0366607 A1* | 11/2021 | Kolluri | .................. G16H 10/65 |
| 2022/0057519 A1* | 2/2022 | Goldstein | ............... G01S 17/88 |
| 2022/0210150 A1* | 6/2022 | Neubauer | ............. H04W 4/022 |

OTHER PUBLICATIONS

Zhe Peng, et al., P2B-Trace: Privacy-Preserving Blockchain-based Contact Tracing to Combat Pandemics. In Proceedings of the 2021 International Conference on Management of Data (SIGMOD '21). Association for Computing Machinery, New York, NY, USA, 2389-2393. (Year: 2021).*
Joseph K. Liu, et. al., Privacy-Preserving COVID-19 Contact Tracing App: A Zero-Knowledge Proof Approach, published in International Conference on Information Security Practice and Experience (ISPEC 2021). Nanjing , China, Dec. 17-19, 2021. (Year: 2021).*

(Continued)

*Primary Examiner* — Vance M Little

(57) ABSTRACT

A method of non-interactive zero-knowledge crowd verifiable digital contact tracing, system and devices that provides improved accuracy and/or privacy by improving the validity of digital contact tracing sources. Private information associated with a respective user intended for a receiver is uploaded to a data server. The receiver is notified that the private information has been uploaded to the data server. A proof of the private information is generated using a proof function of a non-interactive zero-knowledge cryptographic protocol and added to a contact tracing blockchain for the respective user. A second blockchain transaction is added in response to verification of the proof by a verifier network using a verification function of the non-interactive zero-knowledge cryptographic protocol and the receiver is be notified.

20 Claims, 8 Drawing Sheets

(56) References Cited

OTHER PUBLICATIONS

Zero-Knowledge Proofs, Wikipedia, at least as early as Apr. 28, 2022, 16 pages.
Terrence Jo, An Exploration of Zero-Knowledge Proofs and zk-SNARKs, 2019, 21 pages.
Matthew Holroyd, Coronavirus: 'Super-spreaders' of COVID-19 misinformation on Facebook identified, EuroNews, 5 pages, https://www.euronews.com/2020/05/06/coronavirus-super-spreaders-of-covid-19-misinformation-on-facebook-identified Jun. 6, 2020.
Christian Reitwiessner, zkSNARKs in a nutshell, Ethereum Foundation, 15 pages, https://blog.ethereum.org/2016/12/05/zksnarks-in-a-nutshell/ Dec. 5, 2016.
Eli Ben-Sasson, Alessandro Chiesa, Daniel Genkin, Shaul Kfir, Eran Tromer, Madars Virza, Howard Wu, Michael Backes, Manuel Barbosa, Alexander Chernyakhovsky, Dario Fiore, Jens Growth, Joshua A. Kroll, Shigeo Mitsunari, Aleksejs Popovs, Raphael Reischuk, Tadanori Teruya, libsnark: a C++ library for zkSNARK proofs, GitHub.com, https://github.com/scipr-lab/libsnark Jun. 28, 2017.
Eli Ben-Sasson, Alessandro Chiesa, Daniel Genkin, Eran Tromer and Madars Virza, SNARKs for C: Verifying Program Executions Succinctly and in Zero Knowledge (extended version), 53 pages, https://eprint.iacr.org/2013/507.pdf Oct. 10, 2013.
Jens Growth, On the Size of Pairing-based Non-interactive Arguments, IACR-EUROCRYPT-2016, 25 pages, https://eprint.iacr.org/2016/260.pdf May 31, 2016.

\* cited by examiner

METHOD OF NON-INTERACTIVE ZERO-KNOWLEDGE CROWD VERIFIABLE DIGITAL CONTACT TRACING

TECHNICAL FIELD

The present disclosure relates to security and privacy, specifically to digital contact tracing, and more specifically to a method of non-interactive zero-knowledge crowd verifiable digital contact tracing.

BACKGROUND

Contact tracing in public health is the process of identifying persons who may have come into contact with a person having an infectious disease such as COVID-19 (referred to as "contacts") and the collection of information about these contacts. By tracing the contacts of infected individuals, testing the contacts for infection, treating the infected contacts and tracing their contacts in turn, public health aims to reduce infections in the population.

Digital contact tracing is provided by contact tracing applications such as mobile software applications designed to aid contact tracing. Contact tracing applications have been developed and deployed in many countries to address the infectious diseases such as COVID-19. However, accuracy, security and privacy concerns exist with contact tracing applications due to the potential for man-in-the-middle attacks, interception, spoofing, forgery attacks, replay attacks, pranking attacks and other vulnerabilities. For example, with COVID-19 relay pranking, some mobile wireless communication devices can record and replay a "proximity identifier" through their mobile wireless communication device to "prank" victims or, on a greater scale, cause panic in a community. Further, privacy breaching is a significant concern of contact tracing applications even though some contact tracing applications use randomized MAC (Media Access Control) addresses to conceal user identities due to the tracking of user location histories in a centralized repository and other reasons.

Thus, there is a need for digital contact tracing solutions which addresses accuracy, security and/or privacy concerns.

SUMMARY

The present disclosure provides a method of non-interactive zero-knowledge crowd verifiable digital contact tracing, system and devices that provides improved accuracy and/or privacy by improving the validity of digital contact tracing sources. FIG. 5 illustrates an example of a digital contact tracing architecture 300 in accordance with the prior art. Mobile wireless communication devices ("mobile devices") 10 and healthcare centers 310 such as hospitals, infectious disease laboratories, testing facilities or the like, via respective servers (not shown), exchange data with a cloud-based digital contact tracing operator ("Cloud") 320 that provides digital contact tracing via respective servers (not shown). The cloud-based digital contact tracing operator 320 may be a wireless carrier, government entity (such as a public health authority), an application provider, or other entity.

In the shown example, mobile device 10A is associated with a user "Alice" and mobile device 10B is associated with a user "Bob". The mobile devices 10 communicate with each other using a wireless communication protocol such as Bluetooth™ or Wi-Fi™, exchanging digital tracking keys denoted "A" for Alice's key and "B" for Bob's key. Depending on the wireless communication protocol, the mobile devices 10 may communicate directly with each other or indirectly with each other via a communication network 20 such as the Internet. Alice's mobile device 10A sends the digital tracing key's A and B to the cloud-based digital contact tracing operator 320, the key's identifying Alice and Bob, and indicating that Alice and Bob were in contact with each other. Similarly, Bob's mobile device 10B sends the digital tracing key's B and A to the cloud-based digital contact tracing operator 320, the key's identifying Bob and Alice, and indicating Bob and Alice were in contact with each other. The timestamp that the keys were sent or received may be used to determine a time of contact. The cloud-based digital contact tracing operator 320 stores the tracing keys for Alice and Bob for a predetermined period of time—typically set by a public health authority. A healthcare center 310 performs a test on a specimen provided by Alice and determines that Alice is infected with an infectious disease of interest, and subsequently notify the cloud-based digital contact tracing operator 320 of Alice's condition. A time period for contact tracing may be provided by the healthcare center 310 or determined by the cloud-based digital contact tracing operator 320 from the tracing keys for Alice stored by the cloud-based digital contact tracing operator 320 or by other means. The cloud-based digital contact tracing operator 320 determines the Bob was in contact with Alice during the relevant time period and notifies Bob about the contact by sending a message to Bob's mobile device 10B. Bob, upon receiving the notification, can get tested himself, isolate for the required period of time (if necessary), and take any other steps required by public health or desired by Bob in his own self-interest.

It will be appreciated by the foregoing that contact tracing relies on the accurate and timely data sources from healthcare centers which collect and monitor patient information. When a healthcare center 310 sends patient information to the cloud-based digital contact tracing operator 320, it carries private information about the patient. The reliance on the cloud-based digital contact tracing operator 320 to maintain patients' privacy may be a challenge. For example, the cloud-based digital contact tracing operator 320 may accidentally reveal user information. Additionally, the system 300 may be subject to security risks such as false or bogus information being sent to the cloud-based digital contact tracing operator 320 about the health of users, which can the spread of fear.

The present disclosure provides a solution which provides a method of non-interactive zero-knowledge crowd verifiable digital contact tracing which addresses at least some of the accuracy, security and/or privacy concerns of digital contact tracing applications. The method may be implementing using a blockchain storing non-interactive zero-knowledge proofs, the blockchain being maintained by a blockchain network comprising a plurality of nodes, thereby providing blockchain based digital contact tracing. The method uses a non-interactive zero-knowledge proof of knowledge cryptographic protocol. In at least some examples, the non-interactive zero-knowledge proof of knowledge cryptographic protocol may be the ZK-SNARK (Zero-Knowledge Succinct Non-Interactive Argument of Knowledge) cryptographic protocol, which is described in *zkSNARKs in a nutshell* by Christian Reitwiessner, Ethereum Foundation, Dec. 5, 2016, https://blog.ethereum.org/2016/12/05/zksnarks-in-a-nutshell/, and in *On the Size of Pairing-based Non-interactive Arguments* by Jens Growth, May 31, https://eprint.iacr.org/2016/260.pdf., the content of both of these documents being incorporated herein by reference. The digital contact tracing of the present disclosure may be used to achieve verifiable digital contact tracing with zero-knowledge of user identity and zero-knowledge of the information being verified. Advantageously, the solution is privacy preserving. All users can obfuscate information which may indirectly reveal their identity or activity. The obfuscated information may be publicly posted (or published) on a blockchain public ledger, which provides a transparent and untampered storage system. Advantageously, the solution is also non-interactive without any need for interaction between provers and verifiers. With obfuscated information stored on the blockchain public ledger, a verifier need not interact with provers such as users (e.g., Alice and Bob in the above example), the digital contact tracing operator or healthcare centers, thereby reducing the risks of collusion attack or bogus information injections. This is enabled by a non-interactive zero-knowledge cryptographic protocol such as the ZK-SNARK cryptographic protocol which are based on the zero-knowledge principle in which proof of the knowledge of a secret X (e.g., Alice is infected) is shared (e.g., by sharing a hashed value h(X)) without revealing the secret X itself.

In accordance with a first aspect of the present disclosure, there is provided a method performed by a computing of non-interactive zero-knowledge crowd verifiable digital contact tracing, comprising: uploading, from a sending computing device to a data server, private information associated with a respective user, the private information intended for a receiving computing device; causing the receiving computing device to be notified that the private information has been uploaded to the data server; generating, by the sending computing device, a proof of the private information using a proof function of a non-interactive zero-knowledge cryptographic protocol, the proof function receiving a proving key, a public input, and the private information as input; causing a first blockchain record to be added to a contact tracing blockchain for the respective user, the first blockchain record including the proof and the public input; and in response to verification of the proof by a verifier network using a verification function of the non-interactive zero-knowledge cryptographic protocol: causing a second blockchain transaction to a contact tracing blockchain for the respective user, the verification function receiving a verifying key, the public input, and the proof as input, the second blockchain record including an indication the proof has been verified, the verifier network comprising a blockchain network comprising a plurality of node; and causing the receiving computing device to be notified that the proof has been verified.

In some or all examples of the first aspect, the receiving computing device downloads the private information from the data server in response to the receiving computing device being notified that the proof has been verified.

In some or all examples of the first aspect, the method further comprises: causing the receiving computing device to download the private information from the data server in response to the receiving computing device being notified that the proof has been verified.

In some or all examples of the first aspect, the receiving computing device notifies the sending computing device that the private information has been received in response to the receiving computing device downloading the private information from the data server.

In some or all examples of the first aspect, the non-interactive zero-knowledge cryptographic protocol is the Zero-Knowledge Succinct Non-Interactive Argument of Knowledge (ZK-SNARK) cryptographic protocol.

In some or all examples of the first aspect, the proof function is a ZK-SNARK proof function.

In some or all examples of the first aspect, the verification function is a ZK-SNARK verification function.

In some or all examples of the first aspect, the method further comprises: generating by a proving computing device the proving key and the verifying key using a key generation function.

In some or all examples of the first aspect, the key generation function is a ZK-SNARK key generation function.

In some or all examples of the first aspect, the proving key and the verifying key are generated using a tracing key of the respective user.

In some or all examples of the first aspect, the method further comprises: sending the verifying key from the proving computing device to the verifier network.

In some or all examples of the first aspect, the method further comprises: causing a contact tracing blockchain to be created for a respective user for contact tracing for the respective user on a blockchain public ledger.

In some or all examples of the first aspect, the contact tracing blockchain is maintained on a blockchain public ledger.

In some or all examples of the first aspect, the blockchain public ledger is the Ethereum public ledger.

In some or all examples of the first aspect, the proving key and verifying key are based on a function for verifying the private information and a security parameter.

In some or all examples of the first aspect, the private information is associated with an event consisting of the respective user being within a proximity threshold of another user ("a close contact"), a positive infection status of the respective user with respect to an infectious disease, or a close contact between the respective user and another user who has tested positive with an infectious disease ("a positive contact").

In some or all examples of the first aspect, the public input is a timestamp associated with the event.

In some or all examples of the first aspect, the private information indicates that the respective user has been within a predetermined proximity threshold of another user ("a close contact"), a positive infection status of the respective user with respect to an infectious disease, or a close contact between the respective user and another user who has tested positive with an infectious disease ("a positive contact").

In accordance with another aspect of the present disclosure, there is provided a mobile wireless communication device comprising one or more processors, a memory and a communication subsystem. The memory having tangibly stored thereon executable instructions for execution by the one or more processors. The executable instructions, in response to execution by the one or more processors, cause the mobile wireless communication device to perform the methods described above and herein.

In accordance with a further aspect of the present disclosure, there is provided a non-transitory machine-readable medium having tangibly stored thereon executable instructions for execution by one or more processors of a mobile wireless communication device. The executable instructions, in response to execution by the one or more processors, cause the mobile wireless communication device to perform the methods described above and herein.

Other aspects and features of the present disclosure will become apparent to those of ordinary skill in the art upon

DETAILED DESCRIPTION OF EXAMPLE EMBODIMENTS

Figure 1:
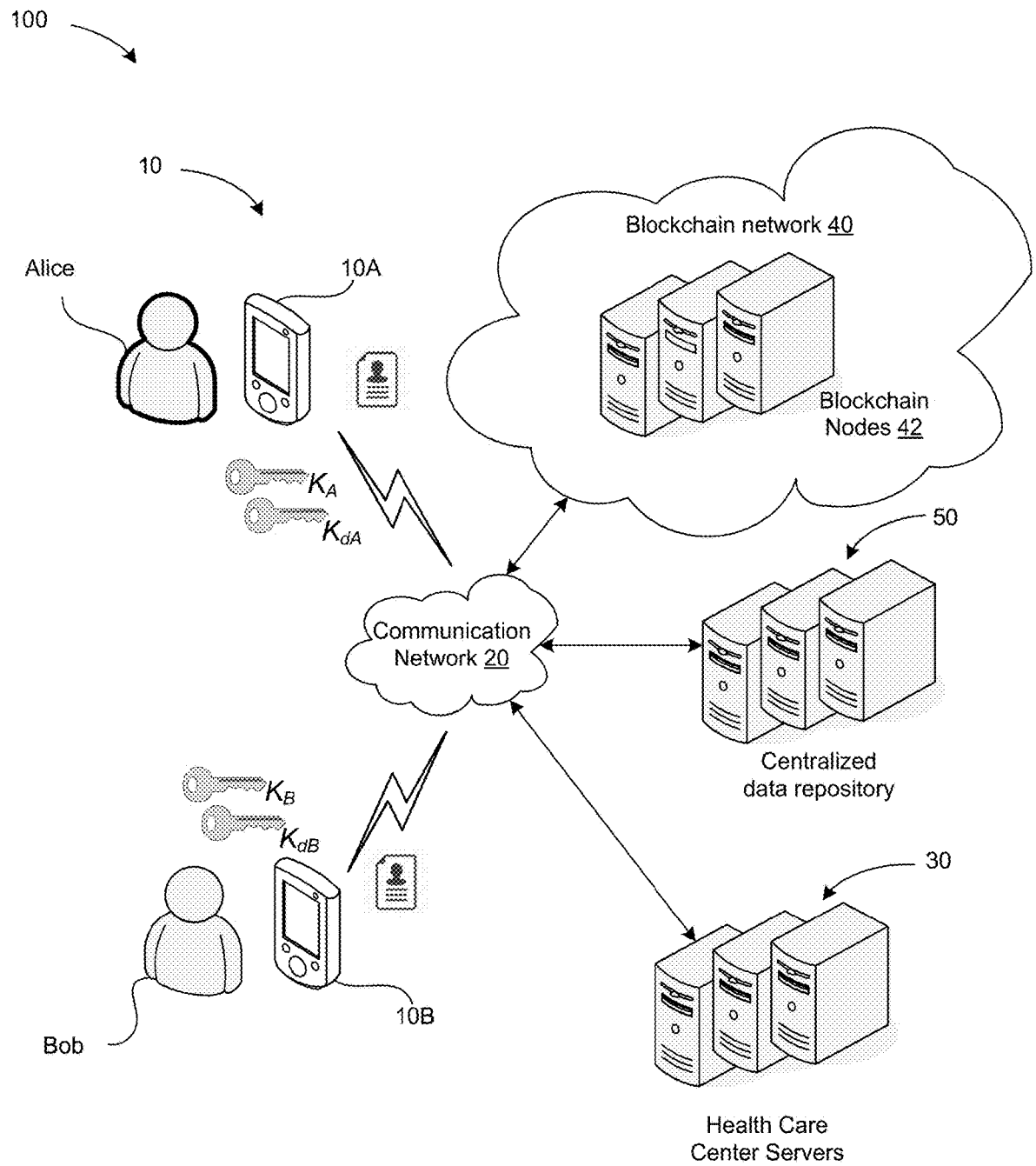
FIG. 1 is a schematic block diagram of a wireless communication system suitable for performing digital contact tracing in accordance with the present disclosure.

The present disclosure is made with reference to the accompanying drawings, in which embodiments are shown. However, many different embodiments may be used, and thus the description should not be construed as limited to the embodiments set forth herein. Rather, these embodiments are provided so that this application will be thorough and complete. Wherever possible, the same reference numbers are used in the drawings and the following description to refer to the same elements, and prime notation is used to indicate similar elements, operations or steps in alternative embodiments. Separate boxes or illustrated separation of functional elements of illustrated systems and devices does not necessarily require physical separation of such functions, as communication between such elements may occur by way of messaging, function calls, shared memory space, and so on, without any such physical separation. As such, functions need not be implemented in physically or logically separated platforms, although such functions are illustrated separately for ease of explanation herein. Different devices may have different designs, such that although some devices implement some functions in fixed function hardware, other devices may implement such functions in a programmable processor with code obtained from a machine-readable medium. Lastly, elements referred to in the singular may be plural and vice versa, except wherein indicated otherwise either explicitly or inherently by context.

Within the present disclosure, the following sets of terms may be used interchangeably: an entity such as a user or operators and a respective computing device of the entity; data and information.

FIG. 1 illustrates a wireless communication system ("communication system") 100 in accordance with an example embodiment of the present disclosure. The communication system 100 comprises a plurality of mobile wireless communication devices ("mobile devices") 10 associated with respective users, a communication network 20 such as the Internet, a plurality of healthcare center servers 30, a blockchain network 40 comprising a plurality of blockchain nodes 42, and a data server 50 managing a data repository. In the shown embodiment, mobile device 10A is associated with a user "Alice" and mobile device 10B is associated with a user "Bob". The mobile devices 10 communicate with each other using a wireless communication protocol such as Bluetooth™ or Wi-Fi™. A wireless communication protocol other than Bluetooth™ or Wi-Fi™ may be used in other embodiments. Other possible wireless communication protocols may include IEEE 802.11, IEEE 802.15.3a (also referred to as UltraWideband (UWB)), Z-Wave, ZigBee, and infrared (e.g., such as an Infrared Data Association (IrDA) communications). Depending on the wireless communication protocol, the mobile devices 10 may communicate directly with each other or indirectly with each other via the communication network 20.

The communications network 112 may be any type of network capable of enabling the mobile devices 10, healthcare center servers 30, blockchain nodes 42 and data server 50 to exchange data including but not limited to a local area network (LAN), such as a wireless local area network (WLAN) such as Wi-Fi™, a wireless personal area network (WPAN) such as Bluetooth™ based WPAN, an intranet, the Internet, a peer-to-peer (P2P) network, a wide area network (WAN), a public-switched telephone network (PSTN), or a public-land mobile network (PLMN) also referred to as a wireless wide area network (WWAN), a cellular network, or a combination of the aforementioned network types coupled via appropriate methods known in the art. The mobile devices 10, healthcare center servers 30, and blockchain nodes 42 may communicate securely using, for example, Transport Layer Security (TLS) or its predecessor Secure Sockets Layer (SSL). TLS and SSL are cryptographic protocols which provide communication security over the Internet. TLS and SSL encrypt network connections above the transport layer using symmetric cryptography for privacy and a keyed message authentication code (MAC) for message reliability. In response to TSL or SSL being used, cryptographic keys for such communication are typically stored in a persistent memory of the respective computing devices.

Figure 2:
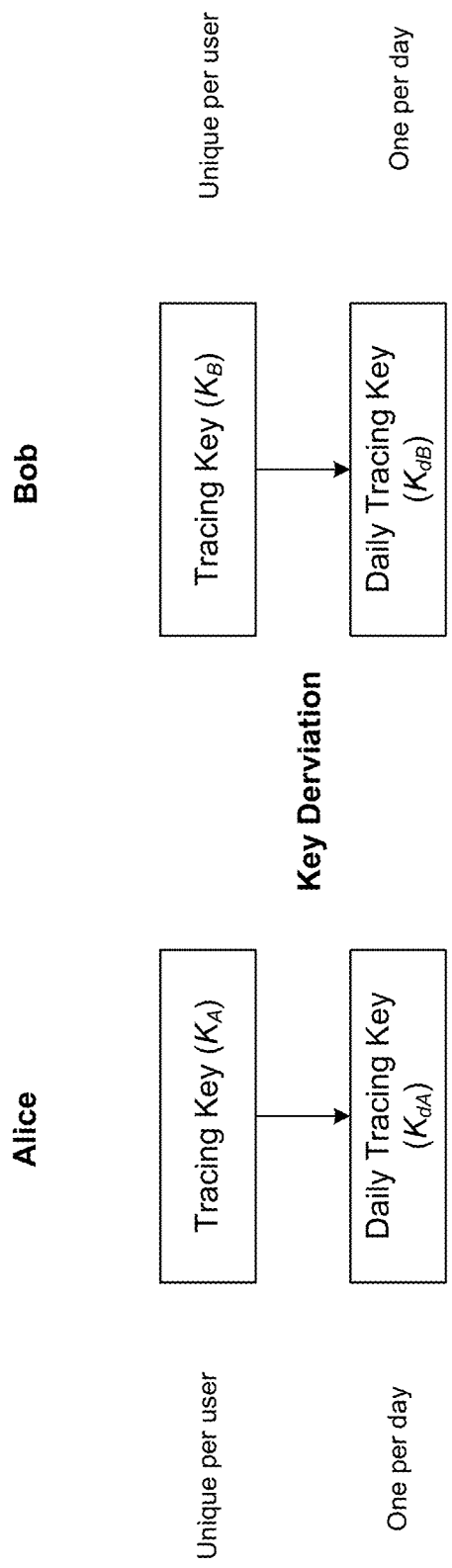
FIG. 2 is schematic block diagram of digital contact tracing key architecture suitable for performing digital contact tracing in accordance with the present disclosure.

The mobile devices 10 each run a digital contact tracing application 160 (FIG. 3) installed thereon that facilities contact tracing. The contact tracing application 160 exchanges data with the data server 50 which stores contact tracing data including, for each user, contact information of other users that each respective user has been in close contact with (i.e., other users that a respective user has been within a predetermined proximity threshold of), positive infection status of each respective user, and positive contacts of each respective user. Referring to FIG. 2, a digital contact tracing key architecture suitable for performing digital contact tracing in accordance with the present disclosure will be described. Each user of the contact tracing application 160 is assigned a unique per user permanent tracing key K which acts as a secure, anonymous identifier. The permanent tracing key assigned to Alice and Bob are denoted $K_A$ and $K_B$, respectively. The permanent tracing keys are generated and provided to the mobile device 10 of each user using a suitable key generation protocol or scheme, examples of which are known in the art and outside of the scope of the present disclosure. For example, a cryptographic random number generator may be used to generate the permanent tracing key. The permanent tracing key is generated using a first key generation (KG) function, also known as a key generator, with public input parameters from the respective computing device such as a device ID and a nonce. The device ID may be a MAC address of a Bluetooth interface of the respective computing device. The key generation (KG) function may be a Key Derivation Function (KDF) such as the Hashed Message Authentication Code (HMAC)-based key derivation function (HKDF) function as defined by IETF RFC 5869 using the Secure Hash Algorithm (SHA)-256 hash function, the content of which is incorporated herein by reference. The key generation protocol or scheme used to generate the permanent tracing keys is set by the contact tracing application 160 so that all permanent tracing keys are generated using the same key generation protocol. The tracing keys $K_A$ and $K_B$ are stored in the memory of the mobile devices 10A and 10B respectively, typically in secure or protected memory which cannot be accessed directly or indirectly by a user. The tracing keys are generated and stored during an initially setup of the contact tracing application 160 or the mobile device 10. The permanent tracing key is not shared or exchanged. The permanent tracing key may be a 32-byte key in some examples.

The permanent tracing key is used to generate a daily tracing key $K_d$ for the respective user. The daily tracing key is generated for each 24-hour period. The daily tracing key also acts as a secure, anonymous identifier similar to the permanent tracing key but by changing regularly, provides additional privacy for the user and protection against various attacks and vulnerabilities. The daily tracing keys for Alice and Bob are denoted $K_{dA}$ and $K_{dB}$ respectively. The daily tracing keys are stored in the memory of the mobile devices 10A and 10B respectively, typically in secure or protected memory with the permanent tracing keys $K_A$ and $K_B$. The daily tracing keys are generated from the permanent tracing keys $K_A$ and $K_B$ using a suitable key generation protocol or scheme, examples of which are known in the art and outside of the scope of the present disclosure. For example, the daily tracing key may be generated from the permanent tracing key by the HKDF function defined by IETF RFC 5869 referred to above. The key generation protocol used to generate the daily tracing keys is set by the contact tracing application 160 so that all daily tracing keys are generated using the same key generation protocol.

The healthcare center servers 30 are application servers that may comprise one or more server modules. The healthcare center servers 30 are operated by hospitals, infectious disease laboratories, testing facilities or the like, and manage infectious disease test results, and notifications for digital contact tracing.

The blockchain nodes 42 are computing devices such as servers, personal computers, or mobile devices 10 running software that connects the respective computing device to a blockchain network 40 that maintains a blockchain public ledger, such as Ethereum. The blockchain nodes 42 perform computing functions that maintain the blockchain public ledger. The blockchain nodes 42 are operated independently of the mobile devices 10 and healthcare center servers 30, typically by different entities.

The data server 50 may provide a single, centralized data repository or several data repositories. The data server 50 is operated independently of the mobile devices 10, healthcare center servers 30, and blockchain nodes 42, typically by different entities. The data server 50 stores contact tracing data for all users. The contact tracing data includes, for each user, contact information of other users that each respective user has been in close contact with (i.e., other users that a respective user has been within a predetermined proximity threshold of) (also known as close contacts), positive infection status of each respective user, and positive contacts of each respective user. The data server 50 stores contact information of users in the form of daily tracing keys. As noted above, the daily tracing key is generated by each user at their mobile device 10. When user come into close contact with each other, they exchange their daily tracing keys locally with each other. Each user then sends the exchanged contact information (i.e., daily tracing key) to the data server 50 via the blockchain public ledger 60 in accordance with the method 800 described below. The daily tracing keys provide contact information that is anonymous and does not publicly expose the name or other personal information of the users. To track the contact information of a user, the user must consent the sharing of their information, for example, as part of the application installation or setup procedure.

The above-described communication system 100 is provided for the purpose of illustration only. The above-described communication system 100 includes one possible communication network configuration of a multitude of possible configurations. Suitable variations of the communication system 100 will be understood to a person of skill in the art and are intended to fall within the scope of the present disclosure. The teachings of the present disclosure are flexible and capable of being operated in various different environments without compromising any major functionality. In some embodiments, the communication system 100 includes multiple components distributed among a plurality of computing devices. One or more components may be in the form of machine-executable instructions embodied in a machine-readable medium.

Figure 3:
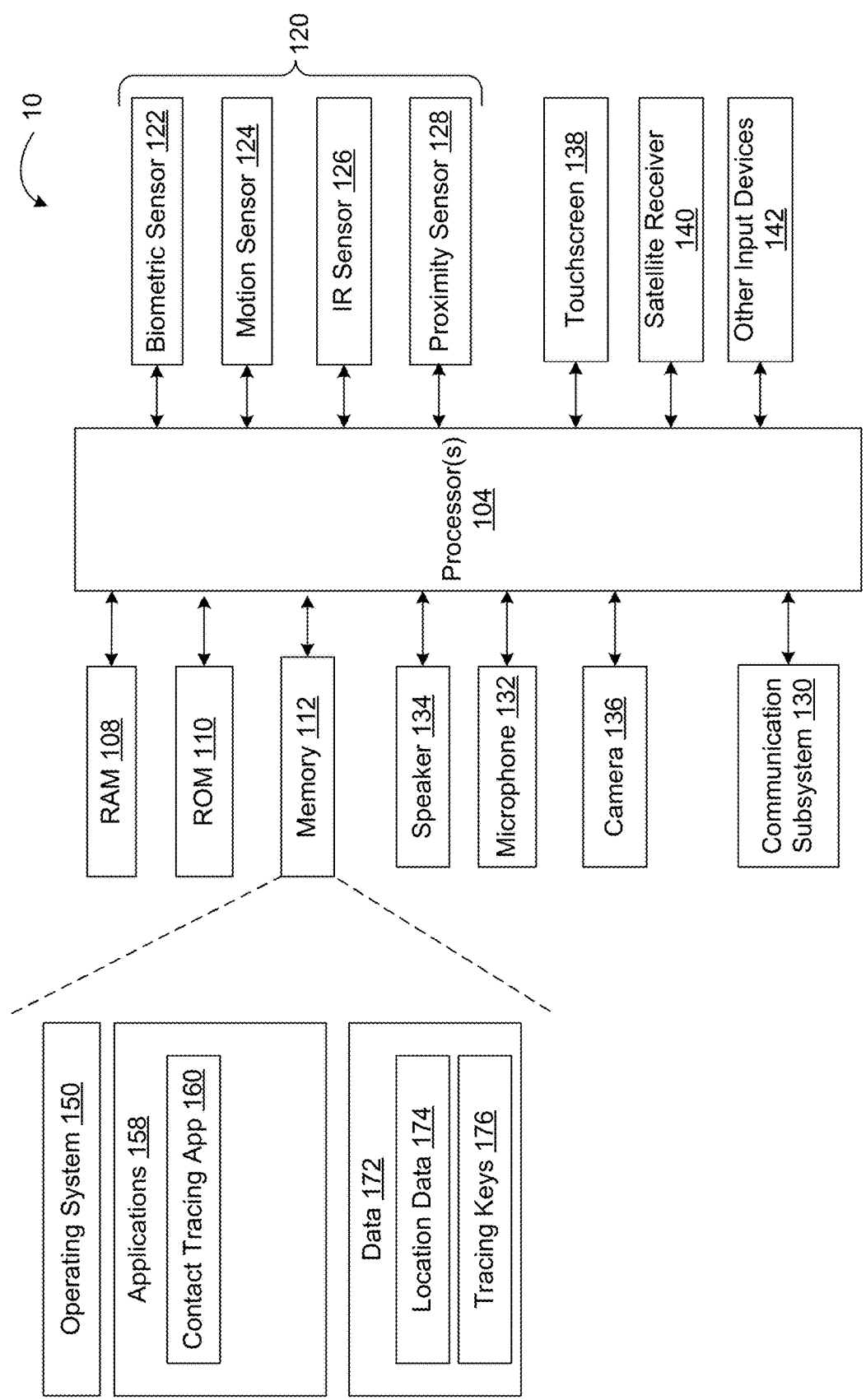
FIG. 3 illustrates a simplified block diagram of an example blockchain node suitable for practicing the teachings of the present disclosure.

Reference is next made to FIG. 3 which illustrates a mobile device 10 suitable for practicing the teachings of the present disclosure. Examples of the mobile device 10 include, but are not limited to, a smartphone or tablet. The mobile device 10 includes one or more processors 202, such as a central processing unit (CPU) with a hardware accelerator, a graphics processing unit (GPU), a tensor processing unit (TPU), a neural processing unit (NPU), a microprocessor, an application-specific integrated circuit (ASIC), a field-programmable gate array (FPGA), a dedicated logic circuitry, a dedicated artificial intelligence processor unit, or combinations thereof. The processors 104 control the overall operation of the mobile device 10. The processors 104 are coupled to a plurality of components via a communication bus (not shown) which provides a communication path between the components and the processors 104. The processors 104 are coupled to Random Access Memory (RAM) 108, Read Only Memory (ROM) 110, and persistent (non-volatile) memory 112 such as flash memory and a communication subsystem 130.

The communication subsystem 130 includes one or more wireless transceivers for exchanging radio frequency signals with wireless networks. The communication subsystem 130 may also include a wireline transceiver for wireline communications with wired networks. The wireless transceivers may include one or a combination of Bluetooth transceiver or other short-range wireless transceiver, a Wi-Fi or other WLAN transceiver for communicating with a WLAN via a WLAN access point (AP), or a WWAN transceiver such as a cellular transceiver for communicating with a radio access network (e.g., cellular network). The cellular transceiver may communicate with any one of a plurality of fixed transceiver base stations of the cellular network within its geographic coverage area. The wireless transceivers may include a multi-band cellular transceiver that supports multiple radio frequency bands. Other types of short-range wireless communication include near field communication (NFC), IEEE 802.15.3a (also referred to as UltraWideband (UWB)), Z-Wave, ZigBee, ANT/ANT+ or infrared (e.g., Infrared Data Association (IrDA) communication). The wireless transceivers may include a satellite receiver for receiving satellite signals from a satellite network that includes a plurality of satellites which are part of a global or regional satellite navigation system.

The mobile device 10 also comprises a microphone 132 and a speaker 134 coupled to the processors 104. The mobile device 10 may also comprise a camera 136, a touchscreen 138, clock (not shown) and a satellite receiver 140 for receiving satellite signals from a satellite network, depending on the type of the mobile device 10. The touchscreen 138 is typically a capacitive touchscreen. The mobile device 10 may also comprise a plurality of sensors 120 coupled to the processors 104. The sensors 120 may comprise a biometric sensor 122 such as face scanner or fingerprint scanner, a motion sensor 124 such as an accelerometer, an infrared (IR) sensor 126, and/or a proximity sensor 128. The sensors 120 may include other sensors (not shown) such as an orientation sensor, electronic compass or altimeter, among possible embodiments. The mobile device 10 may also comprise one or more other input devices 142 such as buttons, switches, dials, a keyboard or keypad, or navigation tool, depending on the type of the mobile device 10.

Operating system software 150 executable by the processing system is stored in the persistent memory 112 but may be stored in other types of memory devices, such as ROM 108 or similar storage element. The operating system software 150 provides a visual user interface (VUI) for user interaction with the mobile device 10 in the form of touch inputs detected via the touchscreen 138 and/or other input devices 142. A number of application programs 158 executable by the processing system are also stored in the persistent memory 112. The application programs 158 comprises a contact tracing application 160. Alternatively, the contact tracing application 160 may be part of the operating system software 150 or an application programming interface (API). The contact tracing application 160 comprises instructions for enabling contact tracing in accordance with the teachings of the present disclosure, such as the method 800 described below.

APIs or other extensions of the contact tracing application 160 enable subroutines or functions of the contact tracing application 160 to be performed when the contact tracing application 160 is not the active or foreground application. The contact tracing application 160 is configured to periodically receive contact information of users in the form of diagnosis keys who have tested positive for an infectious disease even when the contact tracing application 160 is not the active or foreground application. The contact tracing application 160 is also configured to exchange contact information in the form of daily tracing keys to track contacts as described below when the contact tracing application 160 is not the active or foreground application.

The memory 112 stores a variety of data 172, including sensor data acquired by the plurality of sensors 120, including sensor data acquired by the biometric sensor 122, sensor data acquired by the motion sensor 124 (i.e. accelerometer, gyroscope, or inertial measurement unit (IMU) of the mobile device 10), sensor data acquired by the infrared sensor 126, and sensor data acquired by the proximity sensor 128. The memory 112 also stores location data 174 about the location of the mobile device 10 over time, tracing keys 176 (including the permanent tracing key, and daily tracing keys) used by the contact tracing application 160, input data acquired by the touchscreen 138 and/or other input devices 142, user data including user preferences, settings and possibly biometric data about the user for authentication and/or identification, a download cache including data downloaded via the wireless transceivers, and saved files. System software, software modules, specific device applications, or parts thereof, may be temporarily loaded into RAM 108. Communication signals received by the mobile device 10 may also be stored in RAM 108. Although specific functions are described for various types of memory, this is merely one embodiment, and a different assignment of functions to types of memory may be used in other embodiments.

The mobile device 10 may also comprise a battery (not shown) as a power source, such as one or more rechargeable batteries that may be charged, for example, through charging circuitry coupled to a battery interface such as the serial data port. The battery provides electrical power to at least some of the components of the mobile device 10, and the battery interface (not shown) provides a mechanical and electrical connection for the battery.

Figure 4:
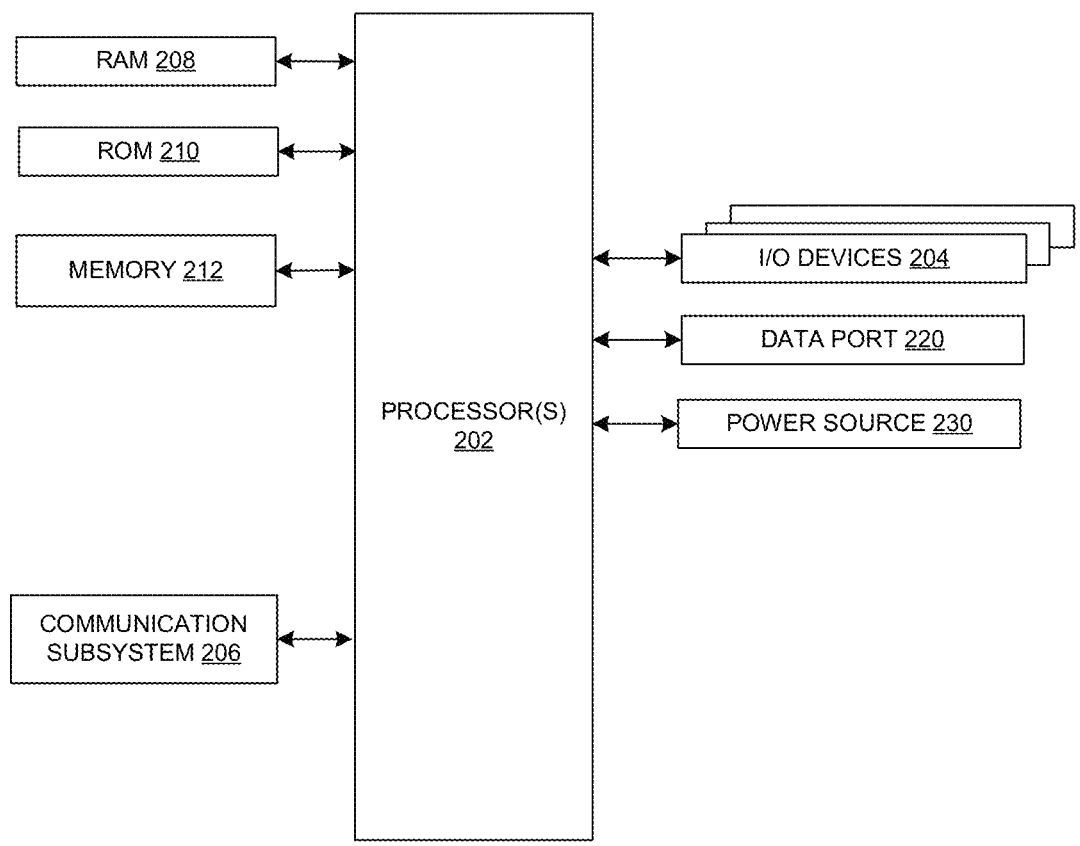
FIG. 4 is a block diagram of an example mobile wireless communication device suitable for practicing the teachings of the present disclosure.
Figure 5:
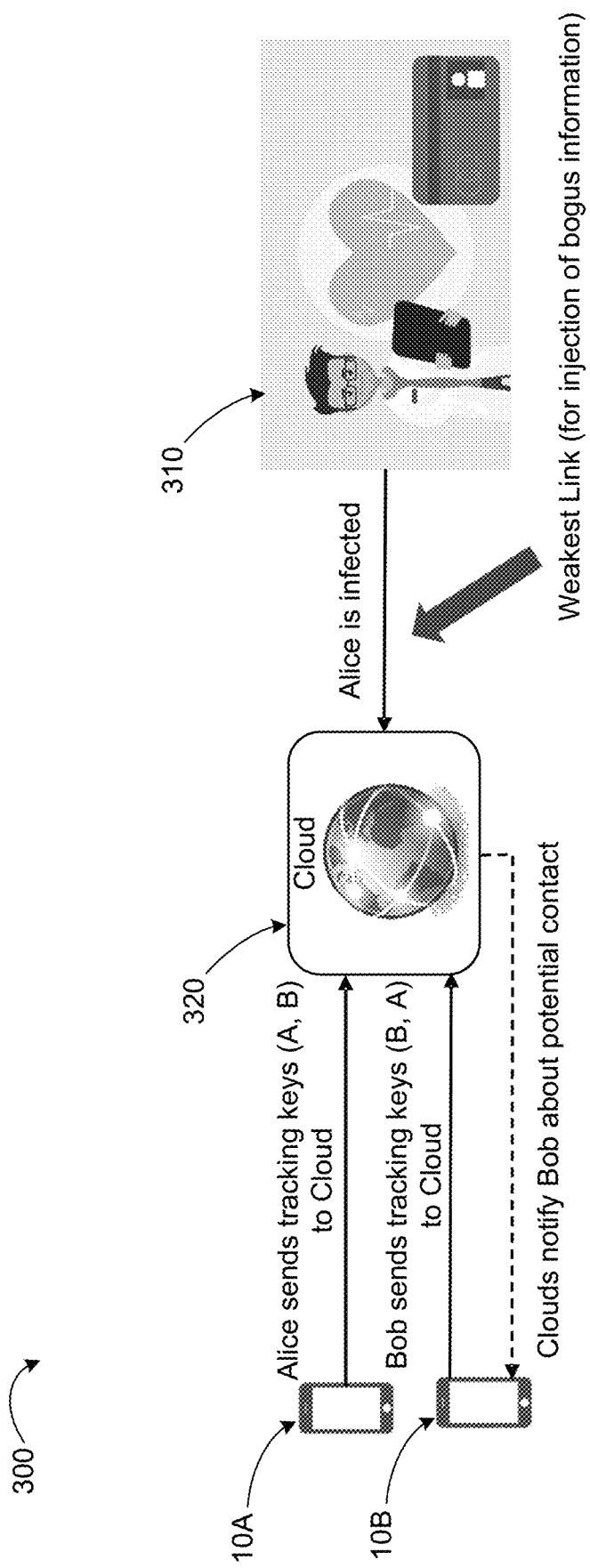
FIG. 5 is schematic block diagram of digital contact tracing architecture in accordance with the prior art.

FIG. 4 illustrates a simplified block diagram of an example blockchain node 40 suitable for practicing the teachings of the present disclosure. The blockchain node 40 includes a processing system comprising one or more processors 104 such as a CPU with a hardware accelerator, a GPU, a TPU, a NPU, an ASIC, a FPGA, a dedicated logic circuitry, a dedicated artificial intelligence processor unit, or combinations thereof. The processors 202 control the overall operation of the computing device 200.

The blockchain node 40 may also include one or more input/output (I/O) devices 204 depending on the nature of the blockchain node 40. Example input devices include a keyboard, a keypad, a touchpad, a mouse, a microphone, sensors, buttons, switches, a camera, and/or a touchscreen. Example output devices include a display, a speaker, a notification light (e.g., LED) and/or a haptic feedback device (e.g., vibrator). In the shown example, the I/O devices 204 are shown as a component of the blockchain node 40. In other examples, the I/O devices 204 may be optional and external to the blockchain node 40. In other examples, the I/O devices 204 may be omitted. The blockchain node 40 may provide a VUI rendered and displayed on an output device such as a touch or non-touch display. A user may interact with the VUI using an input device to access and display relevant information. The blockchain node 40 may also comprise a data port 220 such as a serial data port (e.g., Universal Serial Bus (USB) data port).

The blockchain node 40 includes a communication subsystem 206 that includes one or more network interfaces for wired and/or wireless communication with a communications network (e.g., an intranet, the Internet, a P2P network, a WAN and/or a LAN), mobile device 10, or other blockchain node 40. The network interfaces may include wired links (e.g., Ethernet cable) and/or wireless links (e.g., one or more antennas) for intra-network and/or inter-network communications. The wireless links also for exchanging radio frequency signals with a wireless network that is part of the communication network 112.

The blockchain node 40 includes RAM 208, ROM 210, and non-transitory memory 212 comprising one or more storage units, which may include a mass storage unit such as a solid state drive, a flash memory, a hard disk drive, a magnetic disk drive and/or an optical disk drive. The memory 212 may store instructions for execution by the processors 202 such as instructions to carry out methods described in the present disclosure. The memory 212 may include other software instructions, such as for implementing an operating system and other applications/functions. The memory 212 also stores a variety of data. System software, software modules, specific device applications, or parts thereof, may be temporarily loaded into a volatile store, such as RAM 208, which is used for storing runtime data variables and other types of data or information. Communication signals received by the blockchain node 40 may also be stored in RAM 208. Although specific functions are described for various types of memory, this is merely one example, and a different assignment of functions to types of memory may be used in other embodiments.

In other examples, one or more data sets and/or modules may be provided by an external memory (e.g., an external drive in wired and/or wireless communication with the blockchain node 40) or may be provided by a transitory or non-transitory machine-readable medium. Examples of non-transitory machine-readable media include a RAM, a ROM, an erasable programmable ROM (EPROM), an electrically erasable programmable ROM (EEPROM), a flash memory, a CD-ROM, or other portable memory storage.

The blockchain node 40 also comprises a power source 230, which may include a rechargeable battery that may be charged, for example, through charging circuitry coupled to a battery interface such as a power and/or data port 220.

The blockchain node 40 also comprises a bus (not shown) providing communication among components of the blockchain node 40, including the processors 202, I/O devices 204, communication subsystem 206, RAM 208, ROM 210, and memory 212. The bus may be any suitable bus architecture including, for example, a memory bus, a peripheral bus or a video bus.

Figure 6:
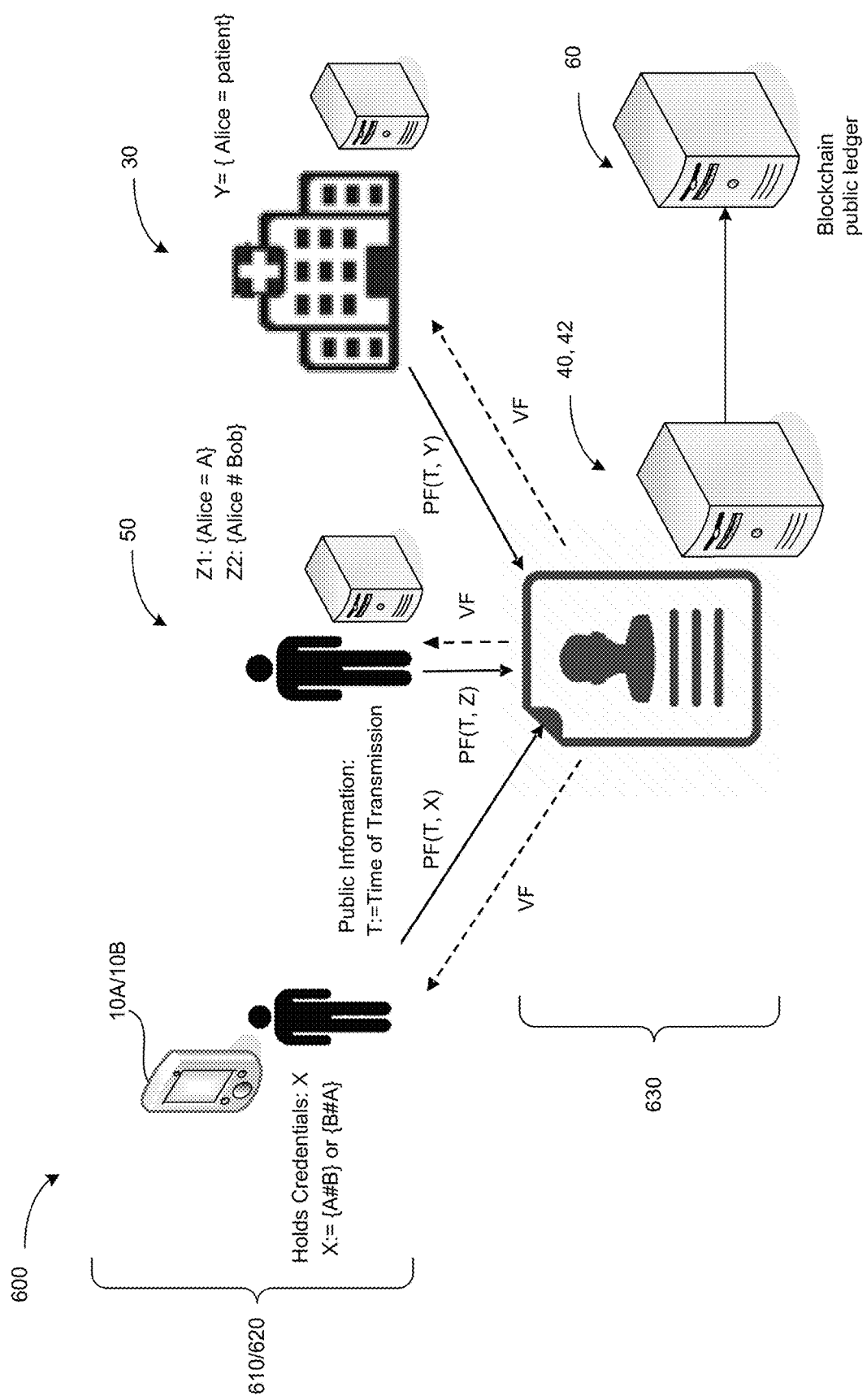
FIG. 6 is a schematic block diagram of a non-interactive crowd verifiable digital contact tracing architecture in accordance with an example embodiment of the present disclosure.
Figure 7:
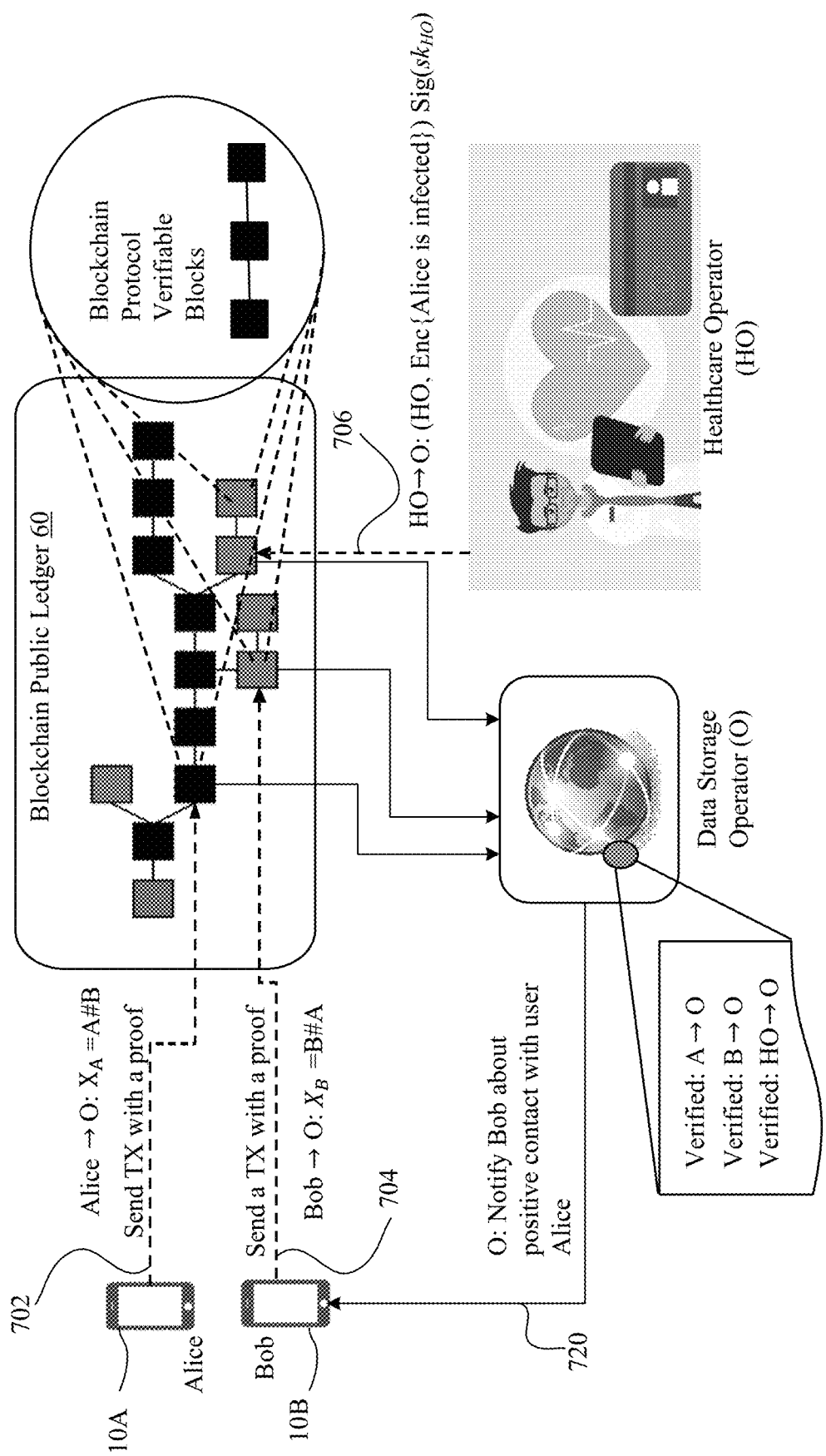
FIG. 7 is a schematic block diagram of an example message sequence in a method of non-interactive crowd verifiable digital contact tracing in accordance with an example embodiment of the present disclosure.

Referring now to FIGS. 6 and 7, a non-interactive crowd verifiable digital contact tracing (NIC-VDCT) architecture 600 in accordance with an example embodiment of the present disclosure will be described. FIG. 6 is a schematic block diagram of the NIC-VDCT architecture 600. FIG. 7 is a schematic block diagram of an example message sequence in a method of non-interactive crowd verifiable digital contact tracing in accordance with an example embodiment of the present disclosure.

The NIC-VDCT architecture 600 is based on a sender-receiver-verifier (SRV) model and the communication system 100 of FIG. 1, which comprises a plurality of mobile devices including mobile devices 10A and 10B belonging to users Alice and Bob, respectively. The NIC-VDCT architecture 600 comprises sending/proving computing devices ("senders") 610, receiving computing devices 620 ("receivers"), and a verifier network ("verifier") 630, at least some of which may not be trusted parties. A sending computing device 610 is an entity that uploads (or sends) private to-be verified information to a third party data server 50 for downloading/retrieval (or receipt) by a receiving computing device 620. The receiving computing device 620 is the intended recipient of the to-be private to-be verified information. The verifier network 630 verifies the private to-be verified information using a non-interactive zero-knowledge cryptographic protocol such as ZK-SNARK. The sending computing device 610 and receiving computing device 620 may each be a mobile device 10, a data server 50, or a healthcare center server 30. The verifier network 630 comprises a blockchain network 40 comprising the blockchain nodes 42. The private to-be verified information may be (i) a close contact of a respective user with another user, wherein the private information comprises a contact ID (tracing key) of the other user and a time of the close contact, which is uploaded by a mobile device 10 of the other user, (ii) a positive infection status of the respective user, wherein the private information comprises a contact ID of the respective user, the positive infection status and a time of the determination of the positive infection status, which is uploaded by a healthcare center server 30, or (iii) or a positive contact of the respective user, wherein the private information comprises a contact ID (tracing key) of the other user and a time of the positive contact, which is uploaded by a data server 50. When the private to-be verified information is verified by the verifier network 630, the private information is downloaded by the receiving computing device 620.

In respect to detecting another mobile device 10 when the other mobile device 10 comes within a predetermined proximity threshold (e.g., when the mobile device 10A of Alice comes within detection range or the mobile device 10B of Bob), contact information comprising the daily tracing key of the other user and a timestamp associated with the timestamp are uploaded from the mobile device 10 of the respective users to the data server 50. A blockchain entry containing a proof for verifying the close contact is added to a contact tracing blockchain for the respective users (e.g., Alice and Bob)—messages/instructions to create the blockchain entry for users Alice and Bob indicated by references 702 and 704 respectively. The daily tracing key of the user Bob and a timestamp are uploaded form the basis of the proof for the user Alice whereas for the user Bob, the daily tracing key of the user Alice and the and a timestamp are uploaded form the basis of the proof for the user Bob. A message concerning the the close contact between users Alice and Bob is also send to the data server 50. If the proof of the private to-be verified information (the close contact between users Alice and Bob) is verified by the verifier network 630, the data server 50 is notified. The data server 50 then processes the private information (e.g., contact information) as appropriate, for example, by updating the contact tracing log for Alice and Bob.

If the proof of the private to-be verified information (the close contact between users Alice and Bob) is not verified by the verifier network 630, the message received by the data server 50 from the mobile devices 10A, 10B is ignored.

The data server 50 stores the daily tracing key of users/mobile devices 10 that a respective user has been in contact with along with the respective timestamp, thereby providing a contact tracing log for each user. The daily tracing key of other users/mobile devices 10 are stored for a predetermined amount of time after which the daily tracing keys are removed or deleted. The predetermined amount of time that the daily tracing keys are stored may be determined by a public health authority, which may be 14 days in some examples.

In response to a positive test result for an infectious disease in respect of a user such as Alice determined by a respective healthcare center server 30, a blockchain entry containing a proof for verifying the positive infection status is added to a contact tracing blockchain for the respective user (e.g., Alice) by the respective healthcare center server 30—a message/instructions to create the blockchain entry for user Alice is indicated by reference 706. A message concerning the positive infection status of Alice is also send to the data server 50.

If the proof of the private to-be verified information (the positive infection status of Alice) is verified by the verifier network 630, the data server 50 processes the private information as appropriate, for example, by updating a database entry for Alice indicating her positive infection status, notifying Alice of her positive infection status, and determining other users who have had contact with Alice during the relevant period in which Alice was infected or infectious using contact tracing logs, the processing of which is described below.

To notify Alice of her positive infection status, the data server 50 sends a message (not shown) to Alice via her mobile device 10A to notify her about her positive infection status. The mobile device 10A receives and processes the message and information contained therein as appropriate, for example, by generating a notification of the positive infection status on the mobile device 10A via an onscreen notification displayed thereon and optionally light and/or audible alert. The onscreen notification may include instructions about what to do next as determined the by relevant public health authority (e.g., isolate, etc.).

If the proof of the private to-be verified information (the positive infection status for the user Alice) is not verified by the verifier network 630, the message received by the data server 50 from the healthcare center server 30 is ignored.

To determine other users who have had contact with Alice during the relevant period in which Alice was infected or infectious using contact tracing logs, the data server 50 determines the daily tracing keys for a threshold number of days that Alice may have been infected. The subset of daily tracing keys for the threshold number of days that Alice may have been infected are referred to as diagnosis keys (or temporary exposure keys). The threshold number of days may be set by a public health authority, which may be 14 days in some examples. The data server 50 uses the contact tracing logs for each user to determine any positive contacts.

In response to a match being found, a blockchain entry containing a proof for verifying the positive contact of Alice for Bob is added to a contact tracing blockchain for the respective user (i.e., Bob) by the data server 50 and a message 720 containing the positive contact and a time of contact based on the associated timestamp (for example, Bob's contact with Alice) is a sent from the data server 50 to the mobile device 10 of the respective user (for example, to Bob on his mobile device 10B). If the proof of the private to-be verified information (the positive contact with infected user Alice for user Bob) is verified by the verifier network 630, the respective mobile device 10B of user Bob processes the private information contained in the message as appropriate, for example, by generating a notification of the positive contact on the mobile device 10B via an onscreen notification displayed thereon and optionally light and/or audible alert. The onscreen notification may include information about the exposure and instructions about what to do next as determined the by relevant public health authority (e.g., isolate, get tested, etc.). The message regarding Bob's exposure is anonymized—Bob does not know which other user was diagnosed (e.g., Alice)—only that he, the user, was in the vicinity of another user who was recently diagnosed with an infectious disease and roughly how long he, the user, was exposed.

If the proof of the private to-be verified information (the positive contact with infected user Alice for user Bob) is not verified by the verifier network 630, the message received by the mobile device 10B of user Bob from the data server 50 is ignored.

It is important to note that the data server 50 does not possess publically identifiable contact information for users such as Alice and Bob. The data server 50 only has addressing information for users' mobile device and a tracing key which identifies users anonymously. The addressing information is typically a device identifier, such as a MAC address, IMEI, etc. rather than a phone number, email address, or other publicly exposed addressing information.

Figure 8:
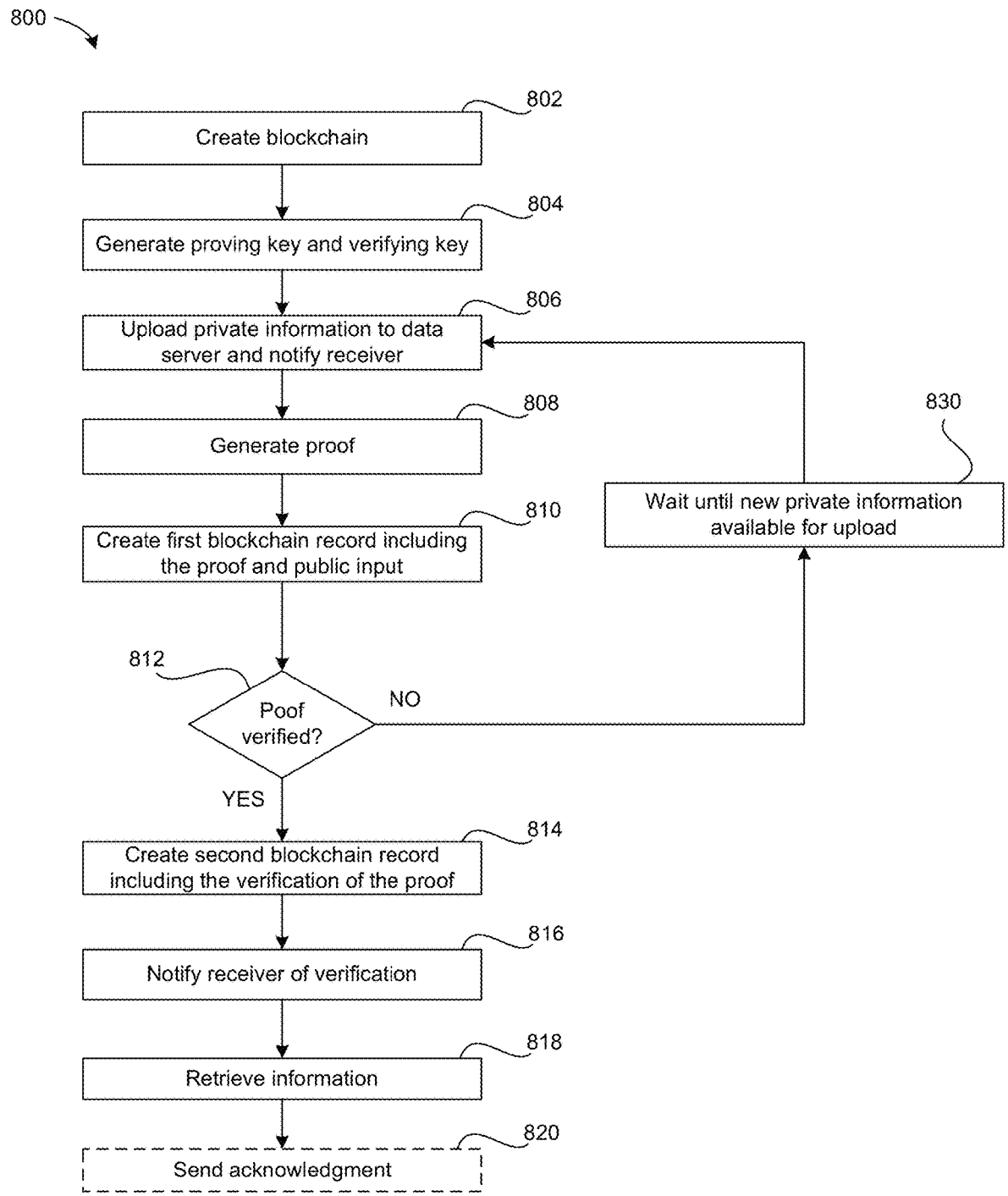
FIG. 8 is flowchart of a method of non-interactive crowd verifiable digital contact tracing in accordance with an example embodiment of the present disclosure.

Referring now to FIG. 8, a method 800 of non-interactive zero-knowledge crowd verifiable digital contact tracing in accordance with an example embodiment of the present disclosure will be described. FIG. 8 is a flowchart of the method 800. The method 800 consists of a setup phase and a use phase. The setup phase begins at step 802. At step 802, a contact tracing blockchain is created for a respective user (e.g., prover) for contact tracing for the respective user on the blockchain public ledger 60 such as Ethereum. A contact tracing blockchain will be created for each user of the method 800. The blockchain is created by the blockchain network 40, i.e., the verifier network 630. The contact tracing blockchain may be a smart contract such as an Ethereum smart contract.

At step 804, a proving key pk and verifying key vk are generated by the computing device of each entity in the system 100 using a second key generation function which receives as input identifying information for the respective entity, a security parameter $\lambda$ that increases with a security strength of an associated cryptographic protocol, and a function C for verifying private information. The second key generation function, also known as a key generator, is a different from the first key generation function used to generate the tracking keys, described above. The second key generation function may be a non-interactive zero-knowledge cryptographic protocol. In some examples, the non-interactive zero-knowledge cryptographic protocol is ZK-SNARK and the key generation function is a ZK-SNARK key generation function. The identifying information may be a tracing key, device ID, user ID, or other identifying information. The function C and the private information to be verified depends on the sender/prover. For example, if the sender/prover is a user/mobile device 10, the private information to be verified may be a user has been in close contact with another user (i.e., Alice has been in close contact with Bob). For another example, if the sender/prover is a healthcare operator/healthcare center server 30, the private information to be verified may be a user is infected with an infectious disease (i.e., Alice is infected with COVID-19). For yet another example, if the sender/prover is a data server operator/data server 50, the private information to be verified may be a user has a potential contacted with a person infected with an infectious disease. Thus, each entity type has a different arithmetic circuit used to verify information. The proving key pk and verifying key vk are specific to the function C for and are generated by a given entity only once for a given function C. The proving key pk is stored locally by the respective computing device of each entity in the system 100 whereas the verifying key vk is shared with the verifier network 630, namely the blockchain nodes 42 of the blockchain network 40. The method comprises sending by each prover the verifying key vk to the verifier network 630.

The use phase begins at step 806. At step 806, a sending computing device 610 uploads private information to the data server 50 and sends a notification to a receiving computing device 620 that the private information has been uploaded. The private information may be a close contact with another user, a positive infection status of the user, or a positive contact of the user.

At step 808, a sending computing device (proving computing device) 610 generates a proof, denoted $\pi$, using a proof generation function (Proof Function), also known as a proof generator, of a non-interactive zero-knowledge cryptographic protocol which receives as input the proving key pk, a public input (or information) x, and private information w (sometimes known as a secret). In some examples, the non-interactive zero-knowledge cryptographic protocol is ZK-SNARK and the proof function is a ZK-SNARK proof function. The private information w is encoded in accordance with the function C and satisfies the function C and is called a witness. Every witness will have a different proof. The proof proves that the sending computing device 610 knows the private information (witness) w and that the private information w satisfies the function C. The proof is generated in accordance with the following equation:

$$\pi = \text{Proof Function}(pk, x, w)$$

The type of private information varies based on the function C. For example, the private information may indicate (i) that the respective user has been within a predetermined proximity threshold of another user ("a close contact") and a time at the close contact occurred, (ii) a positive infection status of the respective user with respect to an infectious disease and a time at the determination occurred, or (iii) a close contact between the respective user and another user who has tested positive with an infectious disease ("a positive contact") and a time at the positive contact occurred. Each of the above types of private information represents an event. For a given type of private information, the private information itself will vary, resulting in a different proof.

The public input may comprise a timestamp T associated with the respective event. The timestamp may comprise a date and time. The public input may also comprise a location or other suitable information.

At step 808, the sending computing device 610 creates a first blockchain record or entry (sometimes referred to as a transaction) in the contact tracing blockchain for the respective user, the first blockchain record including the proof and the public input. The first blockchain record is received by the verifier network 630.

At step 812, the verifier network 630 attempts to verify the proof π using a proof verification function (Verification Function), also known as a proof verifier, of a non-interactive zero-knowledge cryptographic protocol which receives as input the verifying key vk, the public input x, and the proof. In some examples, the non-interactive zero-knowledge cryptographic protocol is ZK-SNARK and the verification function is a ZK-SNARK verification function. The verification function may be represented in accordance with the following equation:

$$\text{Output}(\text{True/False}) = \text{Verification Function}(vk, x, \pi)$$

The Verification Function output or returns "True" if the proof is correct and "False" otherwise. Thus, the Verification Function returns "True" if the prover knows the private information w satisfying C (x, w)==true. It will be appreciated that the Verification Function verifies that the prover knows the private information w by computation—the private information w is never received or considered by the verifier network 630.

If the verifier network 630 verifies the proof in the first blockchain record, the verifier network 630 creates (or adds) a second blockchain record including an indication of the verification in the contact tracing blockchain for the respective user at step 814. Otherwise, the method proceeds to 830 at which the method waits until new private information is available for upload, at which time steps 806-820/830 are repeated.

At step 816, the receiving computing device 620 is notified of the verification of the proof by the verifier network 630 (e.g., blockchain nodes 42). If the receiving computing device 620 does not receive the explicit acknowledgement that the proof has been verified, this means that the receiving computing device 620 should discard the private information uploaded by the sending computing device/proving computing device 610. The receiving computing device 620 is not actively notified of a failure to verify the proof. It will be appreciated that the method 800 can be executed very quickly, in seconds or less, in substantially real-time.

At step 818, the receiving computing device 620 downloads (retrieves) the private information from the data server 50.

At step 820, upon retrieving and/or viewing the private information, the receiving computing device 620 may optionally acknowledge receiving the private information.

The private information is received and processed at the application layer level. In response to the receiving the private information, the private information may be further processed by the receiving computing device 620 causing further actions which depend on the type of private information and the receiving computing device 620. For example, the further processing may comprise downloading by the data server 50 daily tracing keys performed, notifying by the data server 50 a user of a positive infection status via a respective mobile device 10, notifying by the data server 50 a user of a positive contact via a respective mobile device 10, displaying by a mobile device 10 an onscreen notification of a positive infection status, or displaying by a mobile device 10 an onscreen notification of a positive contact. It will be appreciated that the use of the blockchain public ledger in the above-noted methods means that information contained in the records of the blockchain public ledger cannot be modified and that private information concerning the various types of events are not exchanged between users. Users are never informed of the name of close contacts or positive contacts, or of the infections status of other users.

It will be appreciated that the messages described above are application layer messages or device layer messages that are not presented to the user unless otherwise indicated. The only user messages are the onscreen notifications.

The steps (also referred to as operations) in the flowcharts and drawings described herein are for purposes of example only. There may be many variations to these steps/operations without departing from the teachings of the present disclosure. For instance, the steps may be performed in a differing order, or steps may be added, deleted, or modified, as appropriate.

General

Through the descriptions of the preceding embodiments, the present invention may be implemented by using hardware only, or by using software and a necessary universal hardware platform, or by a combination of hardware and software. The coding of software for carrying out the above-described methods described is within the scope of a person of ordinary skill in the art having regard to the present disclosure. Based on such understandings, the technical solution of the present invention may be embodied in the form of a software product. The software product may be stored in a non-volatile or non-transitory storage medium, which can be an optical storage medium, flash drive or hard disk. The software product includes a number of instructions that enable a computing device (personal computer, server, or network device) to execute the methods provided in the embodiments of the present disclosure.

All values and sub-ranges within disclosed ranges are also disclosed. Also, although the systems, devices and processes disclosed and shown herein may comprise a specific plurality of elements, the systems, devices and assemblies may be modified to comprise additional or fewer of such elements. Although several example embodiments are described herein, modifications, adaptations, and other implementations are possible. For example, substitutions, additions, or modifications may be made to the elements illustrated in the drawings, and the example methods described herein may be modified by substituting, reordering, or adding steps to the disclosed methods.

Features from one or more of the above-described embodiments may be selected to create alternate embodiments comprised of a subcombination of features which may not be explicitly described above. In addition, features from one or more of the above-described embodiments may be selected and combined to create alternate embodiments comprised of a combination of features which may not be explicitly described above. Features suitable for such combinations and subcombinations would be readily apparent to persons skilled in the art upon review of the present disclosure as a whole.

In addition, numerous specific details are set forth to provide a thorough understanding of the example embodiments described herein. It will, however, be understood by those of ordinary skill in the art that the example embodiments described herein may be practiced without these specific details. Furthermore, well-known methods, procedures, and elements have not been described in detail so as not to obscure the example embodiments described herein. The subject matter described herein and in the recited claims intends to cover and embrace all suitable changes in technology.

Although the present invention and its advantages have been described in detail, it should be understood that various changes, substitutions and alterations can be made herein without departing from the invention as defined by the appended claims.

The present invention may be embodied in other specific forms without departing from the subject matter of the claims. The described example embodiments are to be considered in all respects as being only illustrative and not restrictive. The present disclosure intends to cover and embrace all suitable changes in technology. The scope of the present disclosure is, therefore, described by the appended claims rather than by the foregoing description. The scope of the claims should not be limited by the embodiments set forth in the examples, but should be given the broadest interpretation consistent with the description as a whole.

The invention claimed is:

1. A method performed by a computing device of non-interactive zero-knowledge crowd verifiable digital contact tracing, comprising:
   uploading, from a sending computing device to a data server, private information associated with a respective user, the private information intended for a receiving computing device;
   causing the receiving computing device to be notified that the private information has been uploaded to the data server;
   generating, by the sending computing device, a proof of the private information using a proof function of a non-interactive zero-knowledge cryptographic protocol, the proof function receiving a proving key, a public input, and the private information as input;
   causing a first blockchain record to be added to a contact tracing blockchain for the respective user, the first blockchain record including the proof and the public input; and
   in response to verification of the proof by a verifier network using a verification function of the non-interactive zero-knowledge cryptographic protocol:
   causing a second blockchain record to be added to a contact tracing blockchain for the respective user, the verification function receiving a verifying key, the public input, and the proof as input, the second blockchain record including an indication the proof has been verified, the verifier network comprising a blockchain network comprising a plurality of nodes; and
   causing the receiving computing device to be notified that the proof has been verified.

2. The method of claim 1, wherein the receiving computing device downloads the private information from the data server in response to the receiving computing device being notified that the proof has been verified.

3. The method of claim 2, wherein the receiving computing device notifies the sending computing device that the private information has been received in response to the receiving computing device downloading the private information from the data server.

4. The method of claim 1, further comprising:
   causing the receiving computing device to download the private information from the data server in response to the receiving computing device being notified that the proof has been verified.

5. The method of claim 1, wherein the non-interactive zero-knowledge cryptographic protocol is the Zero-Knowledge Succinct Non-Interactive Argument of Knowledge (ZK-SNARK) cryptographic protocol.

6. The method of claim 5, wherein the proof function is a ZK-SNARK proof function.

7. The method of claim 5, wherein the verification function is a ZK-SNARK verification function.

8. The method of claim 1, further comprising:
   generating by a proving computing device the proving key and the verifying key using a key generation function.

9. The method of claim 8, wherein the key generation function is a ZK-SNARK key generation function.

10. The method of claim 8, wherein the proving key and the verifying key are generated using a tracing key of the respective user.

11. The method of claim 8, further comprising:
    sending the verifying key from the proving computing device to the verifier network.

12. The method of claim 1, further comprising:
    causing a contact tracing blockchain to be created for a respective user for contact tracing for the respective user on a blockchain public ledger.

13. The method of claim 1, wherein the contact tracing blockchain is maintained on a blockchain public ledger.

14. The method of claim 13, wherein the blockchain public ledger is the Ethereum public ledger.

15. The method of claim 1, wherein the proving key and verifying key are based on a function for verifying the private information and a security parameter.

16. The method of claim 15, wherein the private information is associated with an event consisting of the respective user being within a proximity threshold of another user ("a close contact"), a positive infection status of the respective user with respect to an infectious disease, or a close contact between the respective user and another user who has tested positive with an infectious disease ("a positive contact").

17. The method of claim 16, wherein the public input is a timestamp associated with the event.

18. The method of claim 1, wherein the private information indicates that the respective user has been within a predetermined proximity threshold of another user ("a close contact"), a positive infection status of the respective user with respect to an infectious disease, or a close contact between the respective user and another user who has tested positive with an infectious disease ("a positive contact").

19. A computing device, comprising:
one or more processors;
a communication subsystem coupled to the one or more processors;
wherein the one or more processors are configured to:
upload, to a data server, private information associated with a respective user, the private information intended for a receiving computing device;
cause the receiving computing device to be notified that the private information has been uploaded to the data server;
generate a proof of the private information using a proof function of a non-interactive zero-knowledge cryptographic protocol, the proof function receiving a proving key, a public input, and the private information as input;
cause a first blockchain record to be added to a contact tracing blockchain for the respective user, the first blockchain record including the proof and the public input;
in response to verification of the proof by a verifier network using a verification function of the non-interactive zero-knowledge cryptographic protocol:
cause a second blockchain record to be added to a contact tracing blockchain for the respective user, the verification function receiving a verifying key, the public input, and the proof as input, the second blockchain record including an indication the proof has been verified, the verifier network comprising a blockchain network comprising a plurality of nodes; and
cause the receiving computing device to be notified that the proof has been verified.

20. A non-transitory machine-readable medium having tangibly stored thereon executable instructions for execution by one or more processors, wherein the executable instructions, in response to execution by the one or more processors, cause the one or more processors to:
upload, from a sending computing device to a data server, private information associated with a respective user, the private information intended for a receiving computing device;
cause the receiving computing device to be notified that the private information has been uploaded to the data server;
generate, by the sending computing device, a proof of the private information using a proof function of a non-interactive zero-knowledge cryptographic protocol, the proof function receiving a proving key, a public input, and the private information as input;
cause a first blockchain record to be added to a contact tracing blockchain for the respective user, the first blockchain record including the proof and the public input;
in response to verification of the proof by a verifier network using a verification function of the non-interactive zero-knowledge cryptographic protocol:
cause a second blockchain record to be added to a contact tracing blockchain for the respective user, the verification function receiving a verifying key, the public input, and the proof as input, the second blockchain record including an indication the proof has been verified, the verifier network comprising a blockchain network comprising a plurality of nodes; and
cause the receiving computing device to be notified that the proof has been verified.

* * * * *